US011865090B2

(12) United States Patent
Galun et al.

(10) Patent No.: US 11,865,090 B2
(45) Date of Patent: Jan. 9, 2024

(54) TUMOR SUPPRESSIVE MICRORNAS FOR CANCER THERAPY

(71) Applicant: Hadasit Medical Research Services and Development Ltd., Jerusalem (IL)

(72) Inventors: Eithan Galun, Har Adar (IL); Hilla Giladi, Mevasseret Zion (IL); Chofit Chai, Nahariya (IL); Nofar Rosenberg, Modi'in (IL); Dayana Yaish, Jerusalem (IL); Zohar Shmuelian, Ma'ale Adumim (IL)

(73) Assignee: HADASIT MEDICAL RESEARCH SERVICES AND DEVELOPMENT LTD., Jerusalem (IL)

( * ) Notice: Subject to any disclaimer, the term of this patent is extended or adjusted under 35 U.S.C. 154(b) by 437 days.

(21) Appl. No.: 16/977,722

(22) PCT Filed: Mar. 6, 2019

(86) PCT No.: PCT/IL2019/050244
§ 371 (c)(1),
(2) Date: Sep. 2, 2020

(87) PCT Pub. No.: WO2019/171375
PCT Pub. Date: Sep. 12, 2019

(65) Prior Publication Data
US 2021/0052523 A1    Feb. 25, 2021

Related U.S. Application Data

(60) Provisional application No. 62/640,060, filed on Mar. 8, 2018.

(51) Int. Cl.
C07H 21/02    (2006.01)
A61K 31/167   (2006.01)
A61P 35/04    (2006.01)
A61P 35/00    (2006.01)

(52) U.S. Cl.
CPC .......... *A61K 31/167* (2013.01); *A61P 35/00* (2018.01); *A61P 35/04* (2018.01)

(58) Field of Classification Search
CPC .......... C12N 15/113; C12N 2310/141
See application file for complete search history.

(56) References Cited

U.S. PATENT DOCUMENTS

2013/0121912 A1    5/2013   Yao

FOREIGN PATENT DOCUMENTS

KR    20130014840 A  *  2/2013  ......... A61K 31/7105
WO    WO 2009/021235 A2 *  2/2009  ........... C12N 15/113

OTHER PUBLICATIONS

Aruna Basu, MicroRNA-375 and MicroRNA-221: Potential Noncoding RNAs Associated with Antiproliferative Activity of Benzyl Isothiocyanate in Pancreatic Cancer, Mar. 27, 2011, Genes & Cancer, 2(2) 108-119 (Year: 2011).*
Machine translation via Clarivate Analytics of KR 20130014840 (Year: 2013).*
Lanaya et al. (Nature Cell Biology, 2014, 16, 10, 972-981).*
Blagotinsek et al. (Current Pharmaceutical Design, 2017, 23, 170-175).*
Slabakova et al. (Cell Death and Disease, 2017, 8, e3100).*
Lee et al. (J Mov Disor, 2017, 10(1), 45-52).*
Adi Harel et al., (2015) Reactivation of epigenetically silenced miR-512 and miR-373 sensitizes lung cancer cells to cisplatin and restricts tumor growth. Cell Death Differ 22(8): 1328-1340.
Basu et al., (2011) MicroRNA-375 and MicroRNA-221: Potential Noncoding RNAs Associated with Antiproliferative Activity of Benzyl Isothiocyanate in Pancreatic Cancer. Genes Cancer 2(2): 108-119.
Chai et al., (2017) Metabolic Circuit Involving Free Fatty Acids, microRNA 122, and Triglyceride Synthesis in Liver and Muscle Tissues. Gastroenterology 153(5): 1404-1415.
Rivkin et al., (2016) Inflammation-Induced Expression and Secretion of MicroRNA 122 Leads to Reduced Blood Levels of Kidney-Derived Erythropoietin and Anemia. Gastroenterology 151(5): 999-1010.
Zhou et al., (2014) MicroRNA-363-mediated downregulation of S1PR1 suppresses the proliferation of hepatocellular carcinoma cells. Cell Signal 26(6): 1347-1354.

* cited by examiner

*Primary Examiner* — Amy H Bowman
(74) *Attorney, Agent, or Firm* — BROWDY AND NEIMARK, PLLC

(57) ABSTRACT

The present invention provides compositions having one or more agents capable of increasing expression of one or more endogenous tumor suppressive mi RNAs in one or more producing cells, such that the endogenous mi RNAs can affect one or more target cancer cells. Further provided are method and uses thereof for treating cancer.

14 Claims, 9 Drawing Sheets

TUMOR SUPPRESSIVE MICRORNAS FOR CANCER THERAPY

FIELD OF THE INVENTION

The present invention relates to methods of treating cancer by upregulating expression of endogenous tumor suppressive microRNA molecules, suitable pharmaceutical compositions and uses thereof.

BACKGROUND OF THE INVENTION microRNAs (miRNAs) are short, non-coding RNA molecules, which are endogenously expressed either ubiquitously or in a tissue-specific manner, and play an important regulatory role in various cellular processes. miRNAs are of about 21 nucleotides in length that are part of a mechanism that regulate posttranscriptional gene expression. In mammals, miRNAs are generally transcribed by RNA polymerase II and the resulting primary transcripts (pri-miRNAs) contain local stem-loop structures that are cleaved in the nucleus. The product of this cleavage is one or more precursor miRNA (pre-miRNA). Pre-miRNAs are usually 70-90 nucleotides long with a strong stem-loop structure containing a 2 nucleotides overhang at the 3' end. The pre-miRNA is transported to the cytoplasm by where the Dicer enzyme, which is an endoribonuclease of the RNase III family, further cleaves the pre-miRNA to release a 21 bp dsRNA, the miRNA duplex. The mature miRNA guides RISC to a target site within mRNAs. If the target site has perfect complementarity to the mature miRNA, the mRNA is cleaved at a position that is located about 10 nucleotides upstream from the 3' end of the target site. After the cleavage, the RISC-mature miRNA strand complex is recycled for another activity. If the target site has lower complementarity to the mature miRNA, the mRNA will not be cleaved at the target site but the translation of the mRNA will be suppressed. In humans, there are about 2000 miRs expressed at levels that are expected to have biological significance. Each cell has a very different miR profile. Each gene could be regulated by a number of miRs, and each miR could regulate a number of genes. There are miRs that are expressed in specific cells and there are some that are expressed in a number of cell types. Over 90% of genes are affected by miRs for their expression upon measuring their protein products. Upon stress conditions, as in inflammation or cellular transformation, there is an increase in miRs expression. Various miRs have also been shown to have tumor suppressive effect.

Studies have shown that cells can secrete numerous types of vesicles of different sizes. Some types carry miRs that originate from the same cell source as the vesicles themselves. Exosomes are one specific type of vesicle of the size of 40-100 nm. Studies show that miR-122 produced in the liver targets erythropoietin mRNA in the kidney reducing its protein level in the kidney and blood (Rivkin M, et. al, Gastroenterology 2016; 151:999-1010). Another study has shown the inducement of secretion of miR-122 by free fatty acids (Chofit C. et. al. Gastroenterology 2017 Gastroenterology. 2017 November; 153(5):1404-1415).

Cancer is a leading cause of morbidity and mortality, however, biomedicine faces a formidable and challenging barrier, the lack of new and effective anti-cancer therapeutics. The cost of developing a new anti-cancer drug is extremely costly and time consuming. The incidence of Hepatocellular carcinoma (HCC), for example, is increasingly causing mortality. There are multiple risk factors that cause chronic liver inflammation that induces the initiation and progression of HCC. The chronic inflammatory process, whether the etiology is infectious, metabolic or genetically based (e.g. Wilson Disease) causes genetic and epigenetic genome wide changes, including genomic instability. Yet, the current therapeutic options are mostly insufficient. They are mainly directed for focal/local HCCs and include liver transplantation, radiofrequency ablation (RFA), trans-arterial chemoembolization (TACE) and surgical resections. Both Sorafenib and Regorafenib improve survival only by a few months and have major side effects. The cost of developing a new anti-cancer drug is extremely costly and time consuming. Furthermore, many tumors develop resistance to the drugs, which can also exhibit major side effects.

Thus, there is a need in the art for selective, efficient and safe treatment of various types of malignant conditions, including treatment of metastases. In particular, there is a need in the art for anti-cancer treatment, which is host-based, thus having fewer side effects, safe for use, cost effective and does not induce tumor resistance and can successfully treat metastases.

SUMMARY OF THE INVENTION

The present invention in embodiments thereof provides advantageous compositions for treating cancer in a safe, robust, and effective manner, with minimal side effects, without inducing tumor resistance and which can treat metastases as well. According to some embodiments, there are provided compositions comprising one or more agents (molecules) capable of increasing/inducing expression of endogenous tumor suppressive miRNAs in one or more producing cells, such that the expressed endogenous miRNAs can affect one or more target cancer cells. In some embodiments, there are provided methods of treating cancer using the agents capable of increasing expression of the endogenous tumor suppressive miRNAs.

According to some embodiments, the compositions and methods disclosed herein are advantageous, as they are host-based nature, and thus are very effecting, exhibiting anti-cancer effects and fewer side effects, with the administered miR-inducer-agent being the only "foreign" element. Additionally, due to the fact that each of the tumor suppressive miR simultaneously targets a number of molecular pathways, as well as multiple steps within a given pathway, it aids in overcoming a major obstacle of cancer therapy, being resistance. Additionally, different miRs can act simultaneously increasing their tumor suppression ability.

According to some embodiments, the present invention is based in part on the effects of tumor suppressive miRs, the intercellular communication systems involving vesicles of different sizes (such as exosomes and Ribonucleic Acid Protein complex (RNPs)) and the advantageous enhancement of the expression and secretion of the specific tumor suppressive miRs in producing cells, and the expansion of their effect on various target cells and tissues. Practically each cell in the body can produce miRNAs and miRNAs delivery vehicles to communicate in an autocrine, paracrine and/or endocrine manner. The delivered miRNA acts on a remote cell upon the uptake of the delivery content of the exosome or other delivery systems of different sizes and nature e.g. RNPs. In this regard, miRNAs are functioning in many cases as "RNA hormones".

According to some embodiments, there is provided a composition comprising one or more agents capable of increasing expression of one or more endogenous tumor suppressive miRNAs in one or more producing cells, such that the endogenous tumor suppressive miRNAs can affect one or more target cancer cells.

In some embodiments, the agent comprises a small molecule, a transcription factor, a drug, or combinations thereof.

In some embodiments, increasing expression includes inducing transcription of the endogenous miRNA(s) in the one or more producing cells.

In some embodiments, the producing cell is a target cell. In some embodiments, the target cell is different than the producing cell. In some embodiments, the target cell resides in a different tissue than the tissue in which the producing cell resides. In some embodiments, the target cell is located at a remote location relative to the producing cell.

In some embodiments, the miRNA may be secreted from the producing cell. In some embodiments, the miRNA may be secreted from the producing cell in apoptotic bodies, RNP, a lipid vesicle or combinations thereof. In some embodiments, the lipid vesicle comprises exosomes.

In some embodiments, the target cancer cells are metastatic cancer cells. In some embodiments, the cancer cells are Hepatocellular carcinoma cells (HCC) or cells derived therefrom.

In some embodiments, the tumor suppressive miRNA may be selected from, but not limited to: miR-16, miR-19a, miR-23a, miR-29c, miR-34, miR-98, miR-99a, miR-101, miR-122, miR-122*, miR-124, miR-125b, miR-126, miR-127, miR-133a, miR-133b, miR-134, miR-143, miR-145, miR-146b, miR-153, miR-154, miR-190a, miR-195, miR-200a, miR-206, miR-214, miR-217, miR-296, miR-302b, miR-320a, miR-338-3p, miR-363-3p, miR-375, miR-379, miR-381, miR-384, miR-429, miR-449, miR-451, miR-486, miR-489, miR-497, miR-503, miR-506, miR-511, miR-542-3p, miR-599, miR-613, miR-718, miR-874, miR-922, and miR-4510. Each possibility is a separate embodiment. In some embodiments, the miRNA is miR-122, miR-134a, or both.

In some embodiments, the agent is a transcription factor agonist, capable of inducing expression or activity of a transcription factor in a producing cell. In some embodiments, the agent is ROR-alpha agonist.

In some embodiments, the cells reside in an organism. In some embodiments, the target cell is in-vitro or ex-vivo. In some embodiments, the producing cell is in-vitro or ex-vivo. In some embodiments, the target cell is in-vivo. In some embodiments, the producing cell is in-vivo. In some embodiments, the target cell and/or the producing cells are harbored in a tissue or organism. In some embodiments, the target cells and the producing cells reside in an organism. In some embodiments, the producing cells are manipulated ex-vivo and administered to affect in-vivo target cells.

In some embodiments, the composition is a pharmaceutical composition comprising one or more excipients. In some embodiments, the pharmaceutical composition is for use in treating cancer in a subject in need thereof.

According to some embodiments, there is provided a method of treating cancer in a subject in need thereof, the method comprising administering a composition comprising one or more agents capable of increasing expression of an endogenous tumor suppressive miRNA in one or more producing cells, such that the endogenous miRNA can affect one or more target cancer cells, thereby treating cancer in the subject.

In some exemplary embodiments, the cancer is Hepatocellular carcinoma (HCC). In some exemplary embodiments, the target cancer cells are metastatic cancer cells.

In some embodiments, there is provided a composition comprising one or more agents capable of increasing expression of an endogenous tumor suppressive miRNA in one or more producing cells, such that the endogenous miRNA affects one or more target cancer cells, for treating cancer in a subject in need thereof.

In some embodiments, there are provided kits comprising one or more agents capable of increasing expression of an endogenous tumor suppressive miRNA in one or more producing cells, such that the endogenous miRNA can affect one or more target cancer cells and instructions for use thereof.

Other objects, features and advantages of the present invention will become clear from the following description and drawings.

BRIEF DESCRIPTION OF THE DRAWINGS

FIGS. 4A-4B show bar graphs demonstrating Luciferase activity. FIG. 4A-Bar graphs showing Luciferase activity of miR-122 reporter constructs (WT or Mutated at RORα binding site (mut)) in Huh7 cells or BNL-1ME, treated for 24 hours with 0.4% DMSO, or with 75 μM lauric acid (LA) or with RORα agonist (10 μM SR1078). Luciferase activity was measured 48 hours post transfection and normalized to *Renilla* Luciferase activity expressed from a co-transfected pRL plasmid. (B) FIG. 4A-Bar graphs showing Luciferase activity of miR-122 reporter plasmid carrying the human AGPAT1-3'UTR (miR-122 target site), or DNMT1 3'-UTR plasmid (negative control) in Huh7 cells. The cells were treated for 24 hours with 0.4% DMSO, or with 75 μM lauric acid (LA) or with RORα agonist (10 μM SR1078). Luciferase activity was measured 48 hours post transfection and normalized to *Renilla* Luciferase activity expressed from a co-transfected pRL plasmid. FIG. 4C—bar graphs showing qRT-PCR analysis of miR-122 and miR-18 in RNA extracted from the medium of Huh7 cells treated with 0.4% DMSO, 75 μM lauric acid (LA) or 1004 RORα agonist (SR1078) for 24 hours. Medium microRNAs levels were normalized to spiked C. elegance miR-39. Data in FIGS. 4A-C is presented as SD+/−error bars. *P<0.05, P<0.01, *P<0.001.

FIG. 8A—bar graphs showing the relative level of miR-122 three hours after injection of SR1078 into mice. DMSO injection was used as control. FIG. 8B—Bar graphs showing the mRNA expression levels of CD24 on hepatic progenitor cells after administration of SR1078 into mice. FIG. 8C—Bar graphs showing relative expression levels of miR-122 in three-month old knockout (KO) MDR mice, 6 hours after injection of SR1078. DMSO is used as injection control. FIG. 8D—Bar graphs showing relative expression mRNA levels of CD24 in three-month old knockout (KO) MDR mice, 6 hours after injection of SR1078. DMSO is used as injection control. Data in FIGS. 8A-D is presented as SD+/−error bars. * is p<0.05;  p<0.01, *p<0.005.

DETAILED DESCRIPTION OF THE INVENTION

Figure 1:
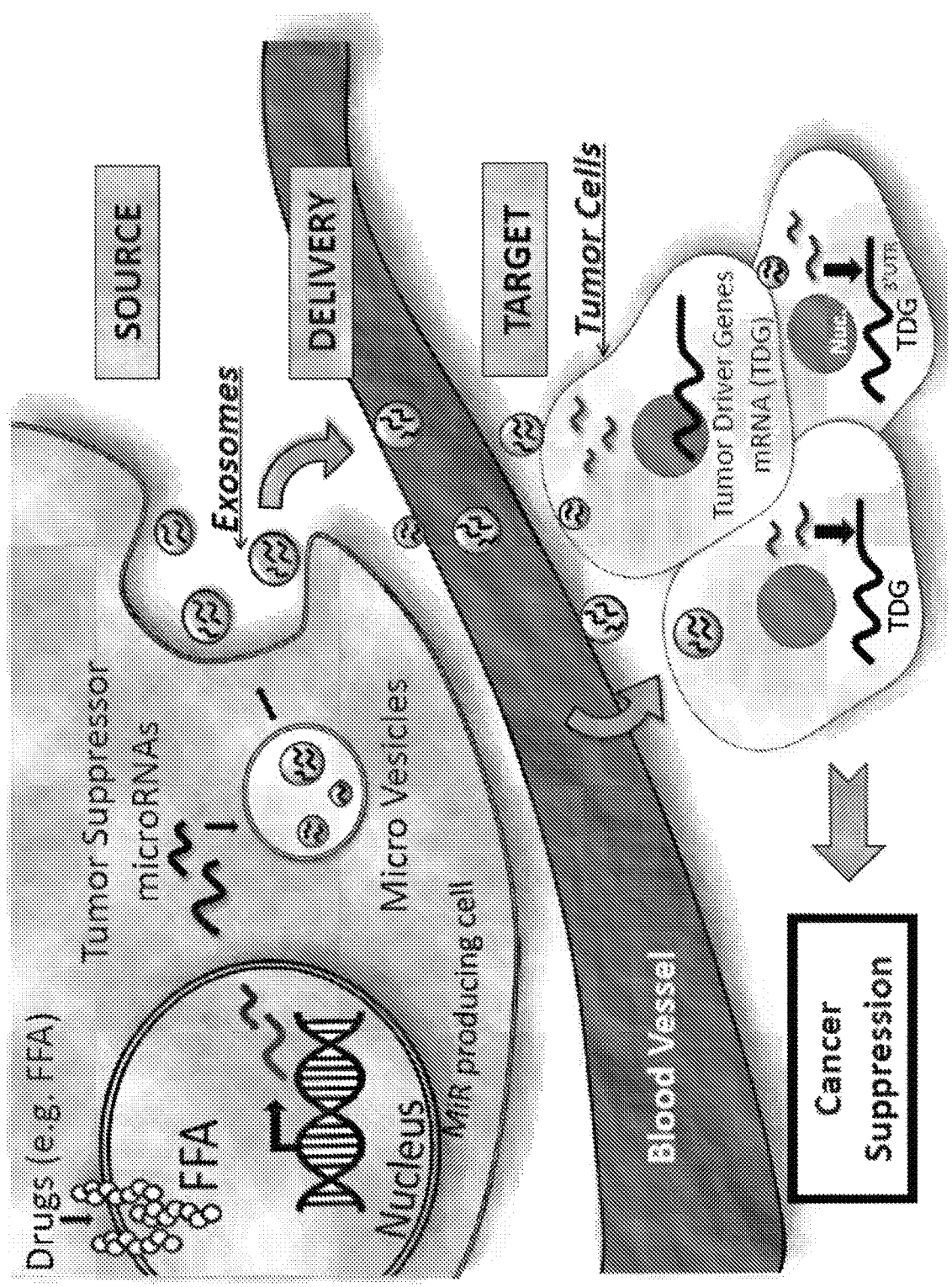
FIG. 1—Schematic illustration of increasing expression of suitable tumor suppressive miRNAs (miRs) in producing cells, by a suitable agent ("Drug"), and secretion of the produced miRs such that they can exert an effect on target cancer cells, to ultimately suppress cancer, according to some embodiments.
Figure 2:
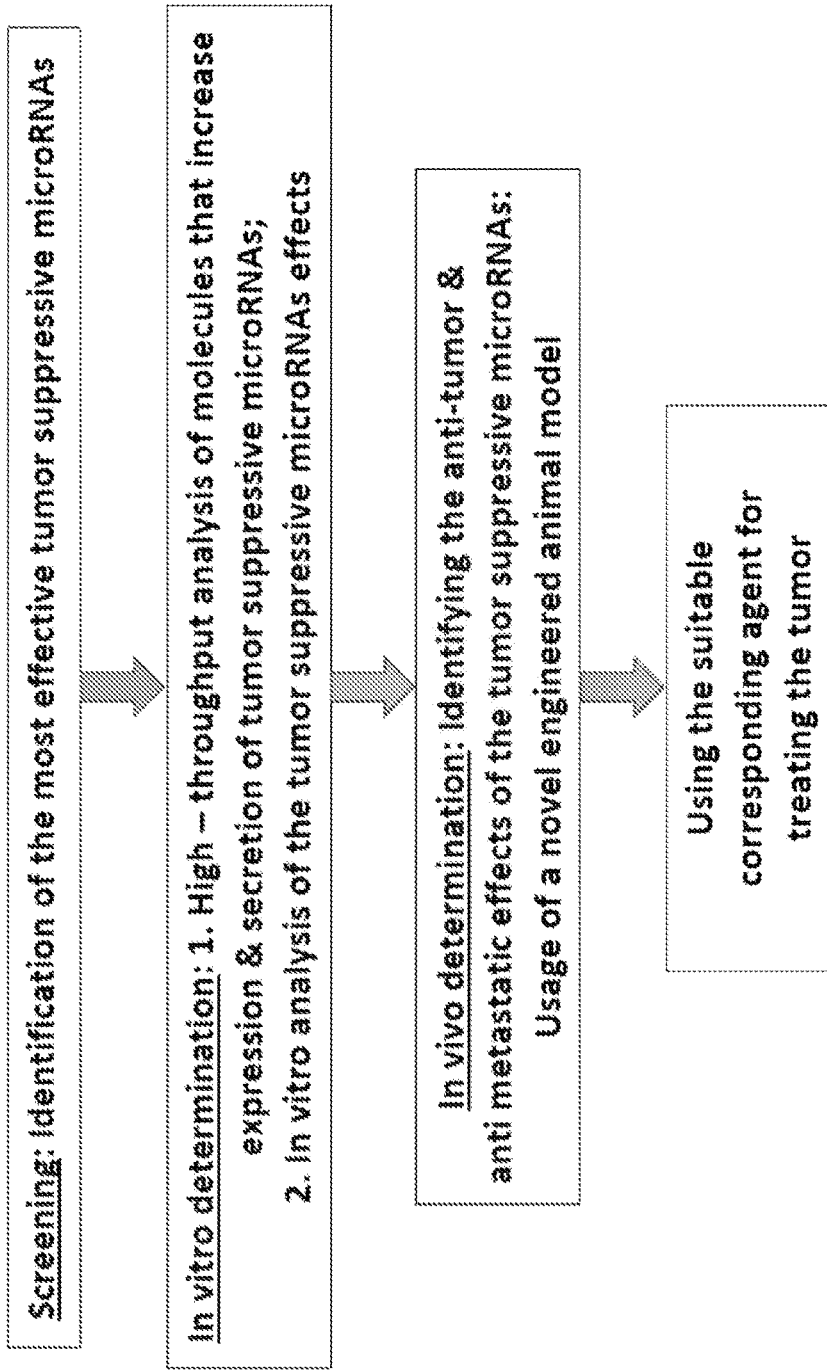
FIG. 2—Schematic illustration of steps in a method of identifying suitable tumor suppressive miRNAs (miRs) in producing cells, and corresponding suitable agents (molecules) capable of increasing the expression of the tumor suppressive miRs in producing cells, to ultimately treat the tumor, according to some embodiments.

According to some embodiments, the present invention provides compositions comprising agents capable of increasing expression of an endogenous tumor suppressive miRNA in one or more producing cells, such that the endogenous miRNA can affect one or more target cancer cells. In some embodiments, there are provided method of treating cancer, the method comprises administrating said compositions.

Definitions

To facilitate an understanding of the present invention, a number of terms and phrases are defined below. It is to be understood that these terms and phrases are for the purpose of description and not of limitation, such that the terminology or phraseology of the present specification is to be interpreted by the skilled artisan in light of the teachings and guidance presented herein, in combination with the knowledge of one of ordinary skill in the art.

The terms "microRNA", "miRNA" and "miR" may interchangeably be used are directed to a small non-coding RNA molecule that can function in transcriptional and posttranscriptional regulation of target genes.

The terms "tumor suppressive miRNA" relates to miRNA that can function as posttranscriptional tumor suppressive regulators and can exert a tumor suppressive effect on target genes or cell.

The term "endogenous" with respect of tumor suppressive miRNA relates to tumor suppressive miRNA molecules that are encoded by the genome of a producing cell and are expressed and optionally secreted from the producing cell. In some embodiments, the endogenous miRNA is not encoded by a foreign nucleic acid introduced into the cell, even if said foreign nucleic acid has been integrated into the genome of the producing cell.

The term "target cell" relates to a cell on which the tumor suppressive miRNA can exert a tumor suppressive effect.

The term "agent" is directed to a molecule that can directly or in-directly increase expression of endogenous tumor suppressive miRNA molecule(s). In some embodiments, the agent can induce expression of miRNA molecules. In some embodiments, the agent is a miR inducer. In some embodiments, the agent can increase transcription of miRNA molecules. In some embodiments, the agent may increase or activate expression of one or more miRNA molecules. In some embodiments, the agent can be increase or activate expression of a specific miRNA molecule. In some embodiments, the agent can act in a cell specific or tissue specific manner. In some embodiments, the agent may be any type of suitable molecule, including, but not limited to, a small molecule, a chemical molecule, a biomolecule (such as, a peptide, a nucleic acid, and the like), a drug, or any combination thereof. Each possibility is a separate embodiment. In some exemplary embodiments, the agent is a molecule capable of activating a transcription factor. In some embodiments, the agent is an agonist.

The term "construct", as used herein refers to an artificially assembled or isolated nucleic acid molecule which may be comprises of one or more nucleic acid sequences, wherein the nucleic acid sequences may be coding sequences (that is, sequence which encodes for an end product), regulatory sequences, non-coding sequences, or any combination thereof. The term construct includes, for example, vectors, plasmids but should not be seen as being limited thereto.

The terms "promoter element", "promoter" or "promoter sequence" as used herein, refer to a nucleotide sequence that is generally located at the 5' end (that is, precedes, located upstream) of a sequence capable of being transcribed ("transcribable") and functions as a switch, activating the expression of a transcribable sequence (which may be a coding sequence). If the transcribable sequence is activated, it is said to be transcribed. Transcription generally involves the synthesis of an RNA molecule (such as, for example, a mRNA or miRNA) from the transcribable sequence. The promoter, therefore, serves as a transcriptional regulatory element and also provides a site for initiation of transcription of.

The terms "Upstream" and "Downstream", as used herein refers to a relative position in a nucleotide sequence, such as, for example, an RNA sequence. As well known, a nucleotide sequence has a 5' end and a 3' end, so called for the carbons on the sugar (deoxyribose or ribose) ring of the nucleotide backbone. Hence, relative to the position on the nucleotide sequence, the term downstream relates to the region towards the 3' end of the sequence. The term upstream relates to the region towards the 5' end of the strand.

As referred to herein, the term "Treating a disease" or "treating a condition" is directed to administering a composition, which comprises at least one agent, effective to ameliorate symptoms associated with a disease, to lessen the severity or cure the disease. Administration may include any suitable administration route.

The term "organism" refers to a mammal. In some embodiments, the organism is human. In some embodiments, the organism is selected from a pet, a rodent, a farm animal, and a lab animal.

The terms "subject", "patient" or "individual" generally refer to a human, although the methods of the invention are not necessarily limited to humans, and should be useful in other mammals.

As used herein the term "small interfering RNA" and "siRNA" are used interchangeably and refer to a nucleic acid molecule mediating RNA interference or gene silencing. The siRNA inhibits expression of a target gene and provides effective gene knock-down.

The term "agonist" refers to an agent (compound, molecule, small molecule, nucleic acid, etc.) that can increase activity or expression of a target molecule (such as a protein).

In some embodiments there is provided a composition that includes one or more agents capable of increasing expression of an endogenous tumor suppressive miRNA in one or more producing cells, such that the endogenous miRNA can affect one or more target cancer cells. In some embodiments, the composition is a pharmaceutical composition. In some embodiments, the pharmaceutical composition may further include one or more suitable excipients.

In some embodiments, the tumor suppressive miRNA may be selected from, but not limited to: miR-34 miR-16, miR-19a, miR-23a, miR-29c, miR-98, miR-99a, miR-101, miR-122, miR-122*, miR-124, miR-125b, miR-126, miR-127, miR-133a, miR-133b, miR-134, miR-143, miR-145, miR-146b, miR-153, miR-154, miR-190a, miR-195, miR-200a, miR-206, miR-214, miR-217, miR-296, miR-302b, miR-320a, miR-338-3p, miR-363-3p, miR-375, miR-379, miR-381, miR-384, miR-429, miR-449, miR-451, miR-486, miR-489, miR-497, miR-503, miR-506, miR-511, miR-542-3p, miR-599, miR-613, miR-718, miR-874, miR-922, and miR-4510. Each possibility is a separate embodiment.

In some embodiments, the miRNA is miR-122. In some embodiments, the miRNA is miR-34.

In some embodiments, the cancer is adrenocortical carcinoma, anal cancer, bladder cancer, brain tumor, brain stem glioma, brain tumor, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, endometrial cancer, esophageal cancer, extrahepatic bile duct cancer, Ewings family of tumors (pnet), extracranial germ cell tumor, eye cancer, intraocular melanoma, gallbladder cancer, gastric cancer, germ cell tumor, extragonadal, gestational trophoblastic tumor, head and neck cancer, hepatocellular carcinoma, hypopharyngeal cancer, islet cell carcinoma, laryngeal cancer, leukemia, acute lymphoblastic, leukemia, oral cavity cancer, cholngiocarcinoma, lung cancer, small cell, lymphoma, AIDS-related, lymphoma, central nervous system (primary), lymphoma, cutaneous T-cell, lymphoma, Hodgkin's disease, non-Hodgkin's disease, malignant mesothelioma, melanoma, merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, or wilms' tumor. In some embodiments, cancer is a non-solid tumor such as a blood cancer.

In some embodiments, cancers include such cancers as: carcinomas, sarcomas, myelomas, leukemias, lymphomas and mixed type tumors. Particular categories of tumors include lymphoproliferative disorders, breast cancer, ovarian cancer, prostate cancer, cervical cancer, endometrial cancer, bone cancer, liver cancer, stomach cancer, colon cancer, lung cancer, pancreatic cancer, cancer of the thyroid, head and neck cancer, cancer of the central nervous system, cancer of the peripheral nervous system, skin cancer, kidney cancer, as well as metastases of all the above. Particular types of tumors amenable to treatment include: hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, squamous cell carcinoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma. Each possibility is a separate embodiment.

According to certain embodiments, the cancer is selected from cervical cancer, hepatic cancer, prostate cancer, breast cancer, skin cancer, colon cancer, lung cancer, pancreatic cancer, lymphoma, myeloma, leukemia, head and neck cancer, kidney cancer, ovarian cancer, bone cancer, hepatocellular carcinoma, cholangiocarcinoma or thyroid cancer. Each possibility is a separate embodiment.

In some embodiments, the cancer is primary hepatic cancer, such as, HCC. In some embodiments, the cancer is pancreatic cancer.

In some embodiments, the effect of the upregulated endogenous antitumor miRNA is autocrine (i.e., affects the producing cell itself).

In some embodiments, the effect of the upregulated endogenous antitumor miRNA is paracrine (i.e., the target cell is in close proximity to the producing cells, such that, for example, the miRNAs produced in the producing cells are secreted in the extracellular environment and can affect neighboring target cells).

In some embodiments, the effect of the upregulated endogenous antitumor miRNA is endocrine (i.e., the target cells are not in close proximity to the producing cells, such that, for example, the miRNAs produced in the producing cells are secreted into the circulation and can affect remote target cells).

In some embodiments, the upregulated endogenous antitumor miRNAs can move from the cell of production/expression, secreted, and then enter remote target cells to impose their gene regulation effect. In some embodiments, the thus produced miRs are stable in the serum for a prolonged period.

In some exemplary embodiments, the producing cells are hepatocytes. In some embodiments, the producing cells are liver cells. In some embodiments, the target cells are hepatic cancer cells. In some embodiments, the target cells are hepatic progenitor cells. In some exemplary embodiments, the target cells express CD24. In some embodiments, the target cells are pancreatic cells.

In some embodiments, the agent is a transcription factor agonist. In some embodiments, the agent is a ROR agonist, i.e., an agent capable of activating ROR activity and/or expression. In some exemplary embodiments, the agent is a RORalpha (RORα) agonist. In some embodiments, the agent is free fatty acid (FFA).

In some embodiments, the transcription factor may be selected from, but not limited to: HNF1a, HNF3b, HNF4a, C/EBPα, RORα, RORbeta (RORβ), ROR gamma (RORγ), NFkB, PPARγ, Foxhead box D3 protein (FoxD3), STAT3, HNF6, or any combination thereof. Each possibility is a separate embodiment.

In some embodiments, the agent is an agonist of a transcription factor, the transcription actor may be selected from, but not limited to: HNF1a, HNF3b, HNF4a, C/EBPα, RORα, RORβ, RORγ, NFkB, PPARγ, FoxD3, STAT3 and HNF6. Each possibility is a separate embodiment.

Reference is made to FIG. 1, which is a schematic illustration showing increasing expression of suitable tumor suppressive miRNAs (miRs) in producing cells, by a suitable agent ("Drug", shown for example, as free fatty acid (FFA)), and secretion of the produced miRs such that they can exert an effect on target cancer cells, which may be remotely located, to ultimately suppress cancer.

In some embodiments, the agent may be introduced to a cell, a tissue or an organism by any of the methods known in the art. In some embodiments, the agent may be introduced in the form of a composition. In some embodiments the composition is a pharmaceutical composition, comprising one or more suitable excipients. In some embodiments, the agent may be introduced to a cell, tissue or organism in combination with one or more additional reagents. In some embodiments, the agent and the additional reagent may be administered in the same or different composition and they may be administered simultaneously, or sequentially, at any time interval.

In some embodiments, the agent is a nucleic acid in the form of a vector or construct, capable of introducing and expressing the agent in a cell.

According to some embodiments, various delivery systems are known and can be used to transfer/introduce the agents and/or compositions of the invention into cells and tissues. In some embodiments, the agents and compositions of the invention may be suitably formulated for intravenous, intramuscular, subcutaneous, intracervical, intratumoral, or intraperitoneal administration. In such embodiments, the composition may be an immediate release or slow release composition.

In some embodiments, the agents and compositions described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

In some embodiments, where the target cells are in vivo, the agents and composition of the invention can be administered by any convenient protocol. In some embodiments, the agents or compositions of the invention may be fed directly to, injected into, the host organism containing a desired target gene or cell. In some embodiments, the agents of the invention can be incorporated into a variety of formulations (compositions) for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, intratumoral, intracervical, intra-tissue and the like. In pharmaceutical dosage forms, the agents may be administered alone or in appropriate association, as well as in combination, with other pharmaceutically active compounds. In some embodiments, the pharmaceutical dosage forms, may be administered locally, by being disposed or contained in a device.

In some embodiments, the cells are ex-vivo. In some embodiments, the composition may be administered to cells ex-vivo. In some embodiments, suitable producing cells (such as, mesenchymal cells) may be manipulated ex-vivo by the agent to produce a one or more miRNAs and said cells can be administered (for example, by transplantation). In some embodiments such ex-vivo manipulated cells may be implanted in a device that enables only molecules of the size of mature miRNAs to pass.

In some embodiments, there is provided a method of treating cancer in a subject in need thereof, the method comprising administering a composition comprising one or more agents capable of increasing expression of an endogenous tumor suppressive miRNA in one or more producing cells, wherein the producing cells are ex-vivo, and administering said cells to the subject, such that the endogenous miRNA expressed by the producing cells can affect one or more target cancer cells, thereby treating cancer in the subject. In some exemplary embodiments, the producing cells are mesenchymal cells. In some embodiments, the producing cells are transplanted to the subject. In some embodiments, the transplantation is auto-transplantation.

In some embodiments, the agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In some embodiments, the pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public. Those of skill in the art will readily appreciate that dose levels can vary as a function of the specific compound, the nature of the delivery vehicle, and the like. Preferred dosages for a given compound are readily determinable by those of skill in the art by a variety of means.

In some embodiments, the compositions of the invention may be advantageously combined and/or used in combination and/or alternation with other agents which are either therapeutic or prophylactic agents, and different from the subject agents. The compositions may also be advantageously combined and/or used in combination with agents that treat conditions often associated with the treated condition. In certain embodiments, administration in conjunction with the subject compositions enhances the efficacy of such agents.

According to some embodiments, reagents and kits thereof for practicing one or more of the above-described methods are provided. The subject reagents and kits thereof may vary greatly. Typically, the kits at least include one or more agents capable of increasing or inducing expression of one or more endogenous tumor suppressive miRNA molecules in producing cells, as described above. The kits may also include a pharmaceutically acceptable delivery vehicle. In addition to those components, the kits further include instructions for practicing the subject methods.

According to yet another aspect of the invention, there is provided a kit comprising the pharmaceutical composition, essentially as described above, and instructions for use of the kit.

The terms "comprises", "comprising", "includes", "including", "having" and their conjugates mean "including but not limited to". The terms "comprises" and "comprising" are limited in some embodiments to "consists" and "consisting", respectively. The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein the term "about" in reference to a numerical value stated herein is to be understood as the stated value +/−10%.

As used herein, the singular form "a", "an" and "the" include plural references unless the context clearly dictates otherwise. For example, the term "a compound" or "at least one compound" may include a plurality of compounds, including mixtures thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

The following examples are presented in order to more fully illustrate some embodiments of the invention. They should, in no way be construed, however, as limiting the broad scope of the invention.

EXAMPLES

Example 1—Identifying Suitable Tumor Suppressive miRs

To this aim, HCC tumor is used as a model system. To identify the most potent and specific anti tumor miRs, the following experiments are performed:
I) A cell based high-throughput (HTP) screening procedure, utilizing the xCELLigence robotic-based system for HTP analysis is generated: a) to monitor cell growth, 10 stable GFP/Luc-expressing HCC human cell lines are generated in which the CCR5D32 site is targeted with a CRISPR/Cas9 system in all cell lines to insert the expression vector in exactly the same genomic locus to enable a better comparison of effects. The human HCC cells used are: HuH7, HepG2, Hep3B, SKhep1, HepaRG, PLC/PRF/5, FLC4, Hep40, FOCUS, and SNU387. (b). These 10 cell lines are transiently transfected with mimic-miRs, (which are tumor suppressive miRs, including: miR-16, -23a, -29c, -34a, -98, -101, -122, -122*, -124, -125b, -126, -127, -133a, -145, -146b, -153, -154, -190a, -195, -200a, -214, -217, -302b, -320a, -338-3p, -375, -379, -381, -429, -449, -451, -486, -503, -511, -542-3p, and -874). Negative control includes a group of 1-3 scramble miRs without any potential of targeting a known tumor driver gene. Cell growth curves during the first 72 hours (collected at 24, 48 and 72 hrs) are generated in the xCELLigence robot. Viability, cell proliferation and cell death are measured. These measures indicate which miRs have the most effective tumor suppressive effects. (c). The five most effective anti-growth miRs are thus identified and their effect is determined/confirmed by FACS analysis measuring sub-G0 (for apoptosis) and S phase levels (for cell proliferation).
II) A complete human miRs library based on mimic-miRs molecules is screened for tumor suppressive effects. The MISSIOM miR mimic library that includes 1902 human mimic-miRs is used in three stably transfected GFP/Luc-expressing human HCC cell lines of different differentiation levels: HepaRG (well differentiated), HuH7 (moderate) and SK-Hep1 (poorly differentiated). The xCELLigence robotic based system is used for this HTP analysis. As above, the most effective tumor suppressive miRs are identified.

Example 2—Identifying Suitable Agents Capable of Enhancing miRs Expression

MiRs are usually expressed from individual Pol II promoters and/or are excised out of introns, with many exceptions such as miRs generated in exons. To identify the agents that can increase selected miRs levels most effectively, expression plasmids in which GFP/Luc are expressed from miRs promoters are generated.

The enhancement of miR expression is engineered separately for each selected miR. Luciferase and GFP co-expression constructs with different miR promoter lengths are generated (usually, four for each miR). Stably transfected cells with each of the promoter constructs are then generated. This system allows the high-throughput identification of the preferred agent that enhances each miR's expression. Based on this HTP screening the best hits (usually, 10 hits, based on a readout of GFP/Luc highest expression) are identified. The effect of the identified agents is then tested by performing both a dose escalation and kinetic experiments. The agents exhibiting the lowest effective concentrations (usually 5 candidates) are used in further experiments.

Example 3—Enhancing miR Expression and Secretion

To determine the actual increase in miR expression, evaluation of the following readouts is performed: 1. Assess mature miR levels; 2. Assess pre- and pri-miR levels. This is due to the fact that many times mature levels do not change but precursors do, most probably due to secretion of the mature miRs. 3. Measure miR levels in the medium. These effects are tested in the three HCC cell lines used above (HepaRG, HuH7 and SK-Hep1).

After the most effective agent for each miR is identified, the effect of the agent is further tested, in particular if the agent is found to enhance a suitable transcription factor. The promoter region of each miR is usually under the control of more than one transcription factor. Thus, co-activating more than one transcription factor simultaneously could have a synergistic effect on the expression of a specific miR. By exposing cells to agents, where each activates a different transcription factor on a specific miR promoter, an enhanced miR expression is caused. Further, in some cases, transcription factor agonists based on the identified activators (agents) are prepared, for example, using computation molecular mimicry. This is performed to enhance the effect and also to reduce the concentration of the agonist. The confirmation of the results is performed using digital droplet PCR (ddPCR), which enables measurement of the actual number of miR molecules in each of the above protocols aimed at increasing miRs expression.

Next, the level of miR secretion is tested independently of the miR expression.

Figure 3:
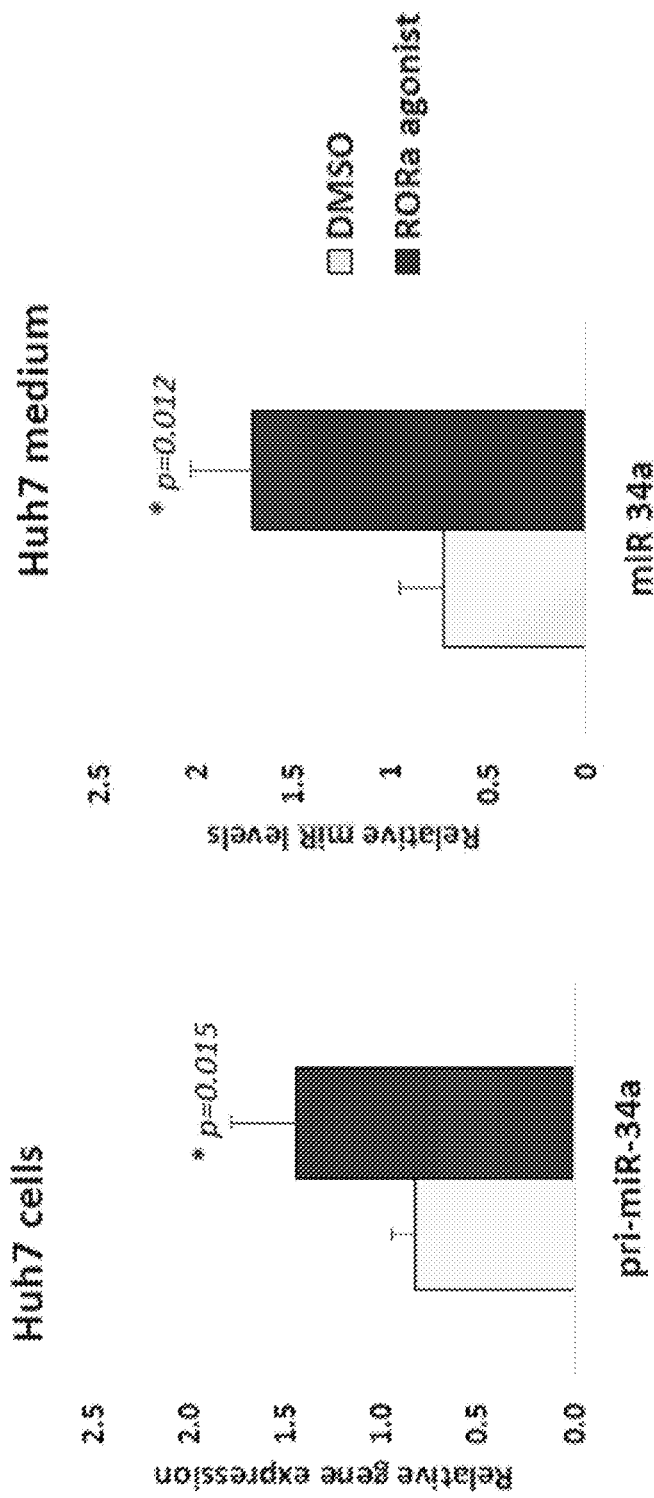
FIG. 3—Bar graphs of experiments showing the effect of a RORα agonist on the expression of pre-miR-34a (left hand panel) and secretion (right hand panel) of miR-34a from HUH7 cancer cells.

Reference is made to FIG. 3, which shows bar graphs of experiments showing the effect of a RORα agonist on expression (left hand panel) and secretion (right hand panel) of miR-34a from HUH7 cancer cells. Huh7 cells treated with ROR-alpha agonist SR1078 (10 µM) overnight (o/n). Upon treatment, primary miR-34a expression levels and mature miR-34a secretion were elevated. miR-34a levels were tested in the cells and in their culture medium using RT-qPCR. The results clearly show elevation in the levels of miR-34a in the cells, as well as a marked elevation of the miR-34a in the external medium, indicating the miR-34a is secreted from the cells.

Figure 4A:
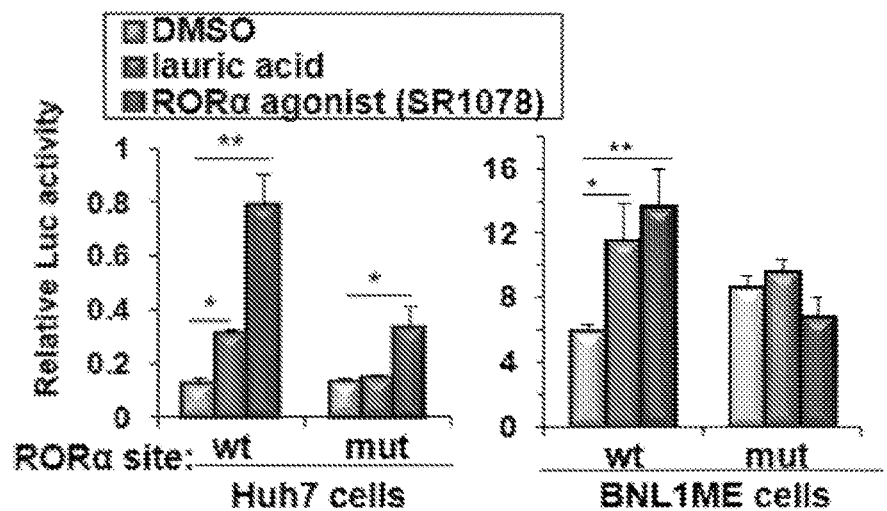
FIGS. 4A-C—Bar graphs showing the in-vitro effect of RORα agonist on the expression and activity of miR-122.
Figure 4B:
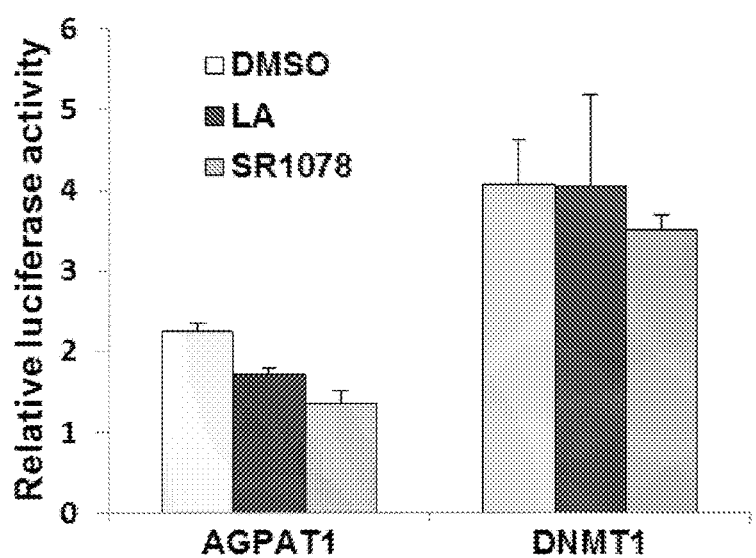
Figure 4C:
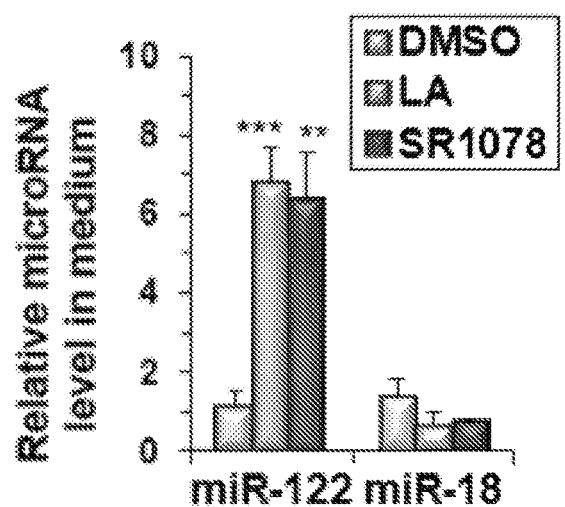

Reference is made to FIGS. 4A-C, which show bar graphs of in-vitro experiments demonstrating the effect of a RORα agonist on expression and activity of miR-122 in HUH7 cells and BNL-1ME cells, which are human and mouse hepatocellular carcinoma cells, respectively. Huh7 cells or BNL-1ME cells were transfected with the reporter constructs PmiR-122-900 (wt) or PmiR-122-900 mutated (mut) at RORα binding site. These constructs harbour about 1 kb of miR-122 promoter sequence (wt or mutated at the ROR alpha binding site), ligated to a luciferase (Luc) reporter gene. As shown in FIG. 4A, incubation of the transfected cells with the ROR-alpha agonist SR1078 (10 µM) overnight (o/n) resulted in activation of the miR-122 promoter, as can be deduced by the increased activity of the reporter gene, Luciferase. Controls included incubation of the cells with 0.4% DMSO (negative control), or with 75 µM Lauric acid (LA), which is a known activator of ROR-alpha. Luciferase activity was measured 48 hours post transfection and normalized to *Renilla* Luciferase activity expressed from a co-transfected pRL plasmid.

Next, Huh7 cells were transfected with a reporter plasmid carrying the human AGPAT1-3'UTR (miR-122 target site) or a negative control reporter plasmid, DNMT1 3'-UTR. Cells were treated for 24 hours with: 0.4% DMSO, or with 75 µM lauric acid (LA) or with RORα agonist (10 µM SR1078) for 24 hours. Presented in FIG. 4B are bar graphs showing the results of the Luciferase assay. Luciferase activity was measured 48 hours post transfection and normalized to *Renilla* Luciferase activity expressed from a co-transfected pRL plasmid. The results clearly indicate that ROR-alpha agonist increased expression of active miRNA (miR-122), which is able to act on its respective target sites (AGPAT1 reporter construct).

Shown in FIG. 4C is qRT-PCR analysis of miR-122 and miR-18 (negative control) in RNA extracted from the medium of Huh7 cells treated with 0.4% DMSO, 75 µM lauric acid (LA) or 10 µM RORα agonist (SR1078) for 24 hours. The microRNA levels in the cells' medium were normalized to spiked C. elegance miR-39. The results indicate that miRNA-122 levels increase in the medium in response to RORα agonist, indicating that miR-122 is expressed and secreted from the cells.

Altogether, the results clearly demonstrate that the expression, activity and secretion into the cell culture medium of miR-122 is dependent on the activation of the promotor of miR-122 by a RORα agonist agent.

Example 4—Determining In Vitro the Tumor Suppressive Effect of miRs

Figure 5:
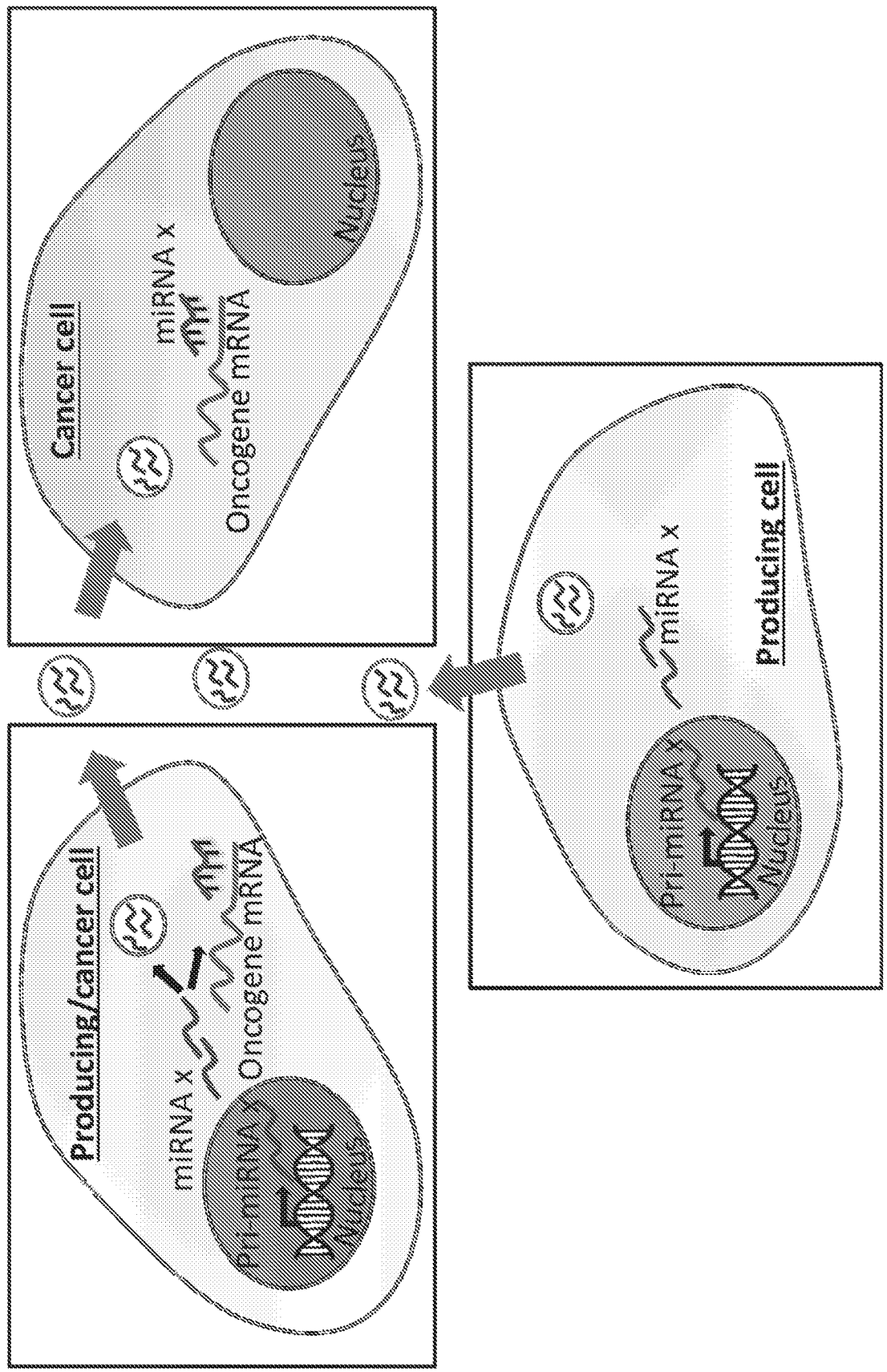
FIG. 5—Schematic illustration of in-vitro tumor suppressing effect, according to some embodiments. miRs are produced either in a tumor cell or a non-cancer cell (producing cells) and can affect the same or remote target cells.

There are two processes by which the selected miRs may exert tumor suppressive effects (FIG. 5): (1). Via enhanced expression of the tumor suppressive miRs within the malignant cells themselves, which may induce tumor cell killing (e.g. apoptosis); or (2). By enhancing the expression and/or secretion of tumor suppressive miRs into the microenvironment and blood, which may suppress remote tumor growth and/or metastasis. These two conditions are modeled in vitro. As illustrated in FIG. 5, miRs are produced either in a tumor cell or a non-cancer cell and can affect the same or remote cells:

Suppressing Tumor Cell Growth by Enhancing the Expression of Tumor Suppressive miRs:

It is assumed that tumor suppressive miRs are expressed at very low levels or not expressed at all in the three HCC cell lines selected for this analysis: HepaRG (well differentiated), HuH7 (moderate) and SK-Hep1 (poorly differentiated). Cell lines expressing high levels of the specific tested miR are excluded, likewise cell lines in which low levels of the tumor suppressive target gene.

A dose response and kinetic analysis for each cell line (one out of three) and miR (one out of five) is performed (at 4 different time points (12, 24, 48 and 72 hours)). This includes establishing in vitro the anti-tumor effect by measuring cell growth, FACS analysis to determine cell cycle populations (in particular, sub-G0 and S phases for proliferation), apoptotic measures, metabolic activity (for example, using Alamar blue staining) and use of surrogate markers for necrosis such as measuring LDH levels. To confirm the specificity of the miR anti-tumor effect, the tumorigenicity of cells transfected with an antagomir, to block the activity of the specific miR are tested. Although the bottleneck for miR's effect is the RISC complex, the effect could be increased by a synergistic tumor suppressive activity.

Figure 6:
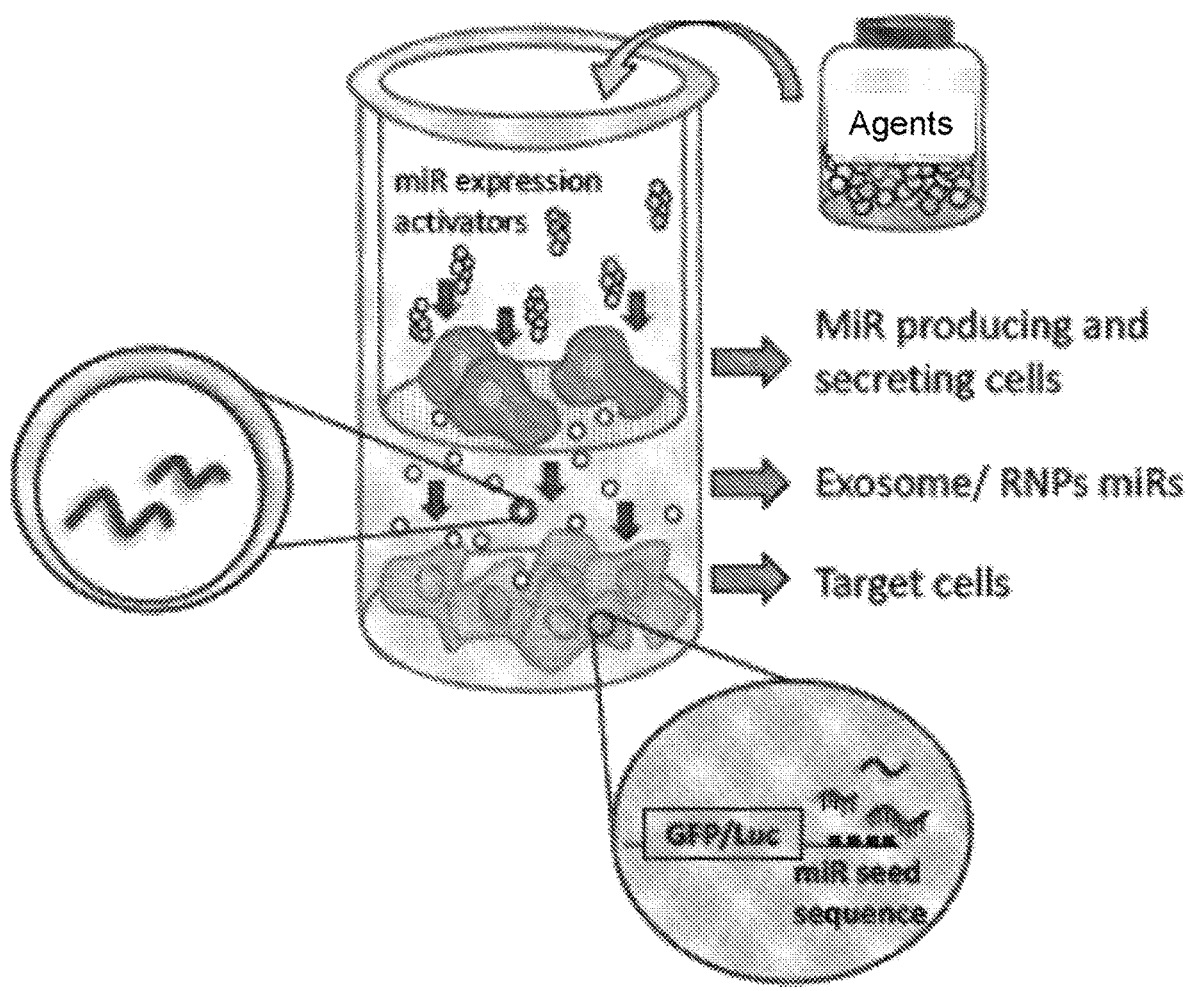
FIG. 6—Schematic illustration of a trans-well system for testing packaging of secreted miRs, according to some embodiments. In the illustrated trans-well system, miRs that are secreted from producing cells situated at the top level, affect target cells located at the bottom chamber.

The paracrine and endocrine impact of anti-tumor miRs on target cells/genes involves packaging of secreted miRs either in ribonuclear protein particles (RNPs) or vesicles, such as, exosomes. To this aim, the trans-well system is used, where miRs secreted from cells situated at the top level, affect target cells located at the bottom chamber (as illustrated in FIG. 6). To ensure that the effect depends on miR secretion, a panel of human HCC cell lines in which the endogenous expression of the tumor suppressive miR is eliminated by CRISPR/Cas-9 genomic region targeting, followed by confirmative sequencing of this ablation. In order to assess the secretory potential of the miR producing cells, condition medium from the producing cells is applied over target cells that harbor a stably transfected miR tester construct. This tester plasmid includes a fragment carrying the recognition motif of the miR seed sequence located down-stream of a GFP/Luc expression vector. If miR targeting takes place, GFP/Luc expression of the tester construct is reduced, indicating that the specific miR has targeted its seed sequence. At this stage, the anti-tumor effects of the secreted miRs are tested in the trans-well system. Protocols for tumor suppressive miR's expression and secretion as detailed above, are applied into the trans-well cell based system, with the designed components illustrated in FIG. 6, i.e. the target cells at the bottom chamber consist of human HCC cells. The tumor suppressive effects are determined by measuring GFP/Luc, cell growth, FACS for cell cycle populations, apoptotic measures, and metabolic activity. This allows identification of the specific secreted miRs with the greatest paracrine/endocrine tumor-suppressive miR effects.

Determination of miR Anti-HCC Effect in a Medium Transfer Model:

The determination includes the following steps: 1. Establishing the tester HCC cells; 2. Selecting the miR producing cells; 3. Measuring the miR effects readouts.

First, HCC tester cell lines are generated. A tester cell line is a cell which is stably expressing GFP/Luc, into which a specific miR seed target sequence is incorporated into its 3'UTR. This is done for each one of the miRs and in each one of the three HCC cell lines (HepaRG, HuH7 and SK-Hep1). For the sake of comparing effects, the constructs are integrated into the CCR5Δ32 site as described above. The secreted miRs effects are assessed by measuring GFP/Luc activity in the tester cell line, after medium transfer of the miRs producing cells after exposing them to the miR activing agents. Next, identification of which cell is an efficient miR producer is performed. In some cases, for each miR, a different producing cell line may be identified. Several tested producing cells include liver derived cells, simulating the liver organ microenvironment, including: 1. Liver parenchymal cells—hepatocytes: The LO1 cells (hTERT transformed); FH-B cells (human fetal hepatocytes); HuS-E/2 (immortalized primary human hepatocytes). 2. Endothelial cells: HUVAC. 3. Macrophages: RAW 264.7 (mouse macrophage); primary Kupffer cells (derived from liver perfused preparation), and 4. Stellate cells: LX2 (human hepatocyte stellate cells). Next, measurable readouts are characterized. For the miR biochemical effect (seed target binding), GFP and Luc are measured. For miR anti-HCC effects, FACS and xCELLigence testing are performed, as described above.

Figure 7:
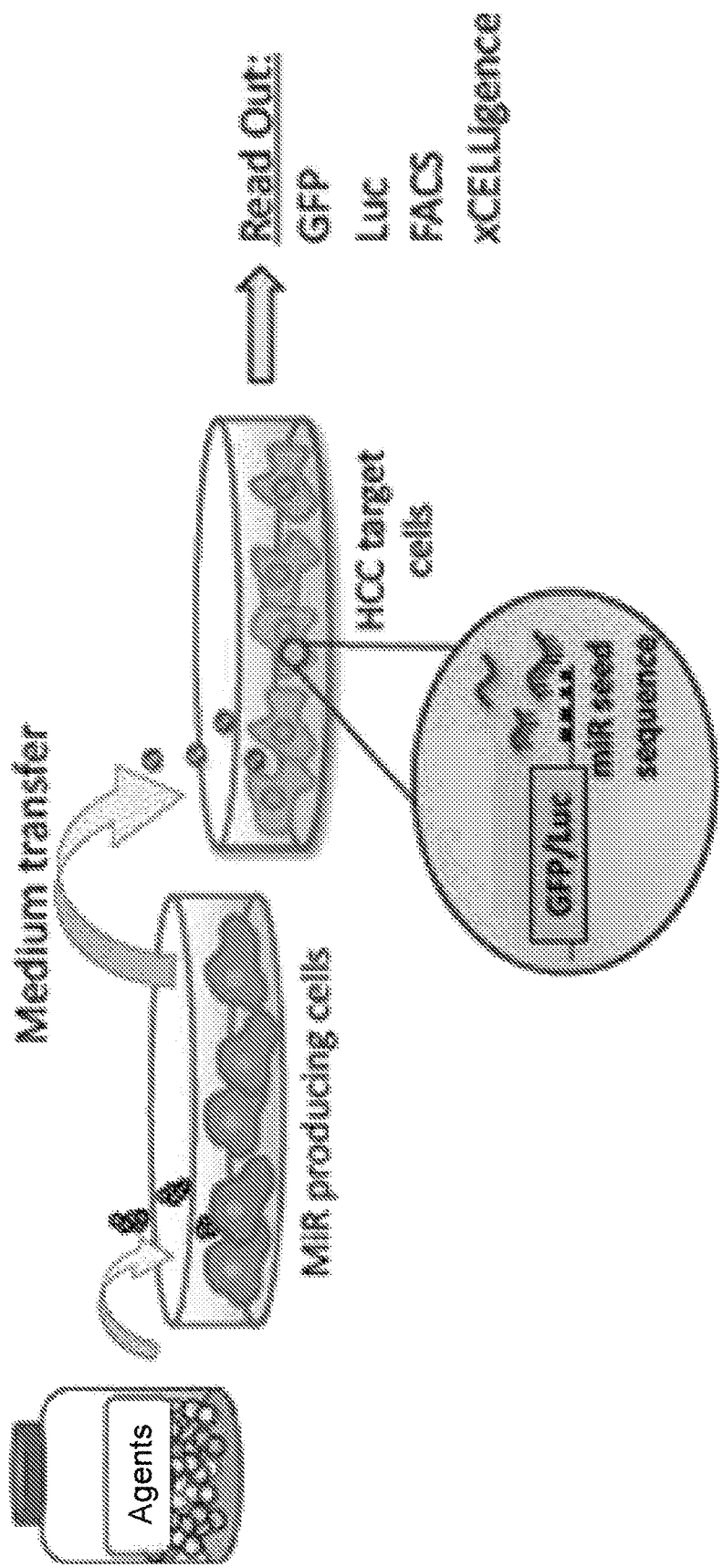
FIG. 7—Schematic illustration of a medium transfer model for determination of tumor suppressing effect of tested miRs on target HCC cells, according to some embodiments.

Each one of the 5 miRs for each one of the producing cells and HCC target cells, and each one of the miR expression activating agent are tested by this experimental protocol (FIG. 7): The suitable agent is added to the miR producing cell. At the indicated time, the medium of this producing cell is applied to the HCC-tester target cell line. The different HCC-tester target cells are assessed for the expression of GFP and Luc as well as analyzed for cell growth, cell cycle, apoptosis and necrosis as described above. This leads to the identification of the most effective miR activator agent and the miR exhibiting the highest anti-HCC effect in vitro.

Example 5—Determining In Vitro the In Vivo Impact of the Tumor Suppressive miRs To determine the in vivo anti-tumor effects of the antitumor miRs and their regulating agents (identified in the examples above herein), several animal models are used. The following are determined (1) Secretion in vivo; (2) In vivo anti-tumor effect and (3) Anti-metastatic effect.

Quantifying the Secretion of the Tumor Suppressive miRs:

The first step in assessing the tumor suppressive effect in vivo is to determine the level and kinetics of miRs secretion.

It appears that non-tumor cells express and secrete higher levels of miRs than cancer cells, such as the case, for example, for the tumor suppressor miR34a, secreted from hepatocytes. To this aim, wild-type (WT) mice are used. In vivo drug escalating doses are tested for those agent identified in vitro (Examples 1-4) to have preferred effects. The number/concentration and kinetics in mice blood of the specific miRs are determined using the digital droplet PCR (ddPCR) system. The secretion is be validated in transgenic mice carrying the GFP/Luc tester system with the specific miR sequence targeted by the miR. The effect is monitored/quantified in an IVIC imaging apparatus. The specific agent and dose thus determined are further used for assessing the tumor suppressive effect in vivo.

In Vivo Measurement of Tumor Suppressive Effects of Secreted miRs on Human HCC Cells:

1. Select for Conserved Tumor Suppressive miRs that Share Identical Transcription Factors in Human and Mouse:

To determine whether the mouse and human miR promotor regions are activated by the same transcription factors the following experiments are performed: a Luc expression vector with the miR promotor region identified above is liver-directed by tail vein injection. This test confirms the expression of the mouse miRs under activated transcription factors in mouse cells. Further, to test whether the mouse mature miRs targets 3'UTR of human genes, one human target gene is selected for each mouse miR tested. The 3'UTR of a putative human target gene of a specific miR is cloned under a GFP/Luc expression vector with a CAG promoter. Two mouse HCC cell lines, BNL1ME (BALB/C) and Hepa1-6 (C57BL) are transfected with the above constructs and activate the relevant miR with the relevant activating agent, to determine the mouse miR effect on the human 3'UTR construct bearing the miR seed target sequences.

2. Determining the Activation and Secretion of miRs In Vivo:

To assess the in vivo effect of miRs, 5 transgenic mice are generated. Each mouse harbors a CAG-GFP/Luc expressing vector with one of the 5 seed targets of miRs in its 3'UTR. The transgene is integrated into the ROSA26 locus to enable comparison between miRs effects. The expression of the transgene is in all tissues. Activating an authentic miR promoter in mouse cells results in suppression of Luc/GFP expression. The activation is performed with the suitable agent identified above. The effect is monitored using in vivo imaging (IVIC imaging system), and confirmed by an analysis including histology and protein quantitation.

The suppression of the expression can result from expression of the miR in the same cell as the transgene, or from miR secreted from a neighboring or a remote cell. The analysis of the harvested tissues in which there was a reduction of expression indicates whether the miR and the transgene effect co-occurred in the same cells. Alternatively, this could be in different cells. To confirm the paracrine or endocrine miR effect, an anti-CD63 or anti-CD9 antibody, or an anti-mouse Ago2 neutralizing antibody are injected to neutralize exosomes or RNPs in the mouse circulation, respectively. This enable to determine the contribution of circulating miR to the reduced expression. In addition to the functional studies described, miR's expression is monitored in mouse tissues. The tissues are selected based on the in vivo results.

3. Determining the miR Tumor Suppressive Effect on HCC Cell Growth In Vivo:

In the in vivo anti-HCC assessment, two models are used:
a). The subcutaneous implantation of human HCC cells: These experiments are conducted in SCID mice (or in NSG mice in case of slow of growth of the human tumor cells). The three cell lines, HepaRG, HuH7 and SK-Hep1, in which all have a GFP/Luc expression vector integrated into the CCR5Δ32 site generated by the CRISPR/Cas9 system are described above. These cells are implanted subcutaneously in SCIDs. After initiation of growth, miR activators are administered to the mice. The miR effect is monitored by assessing imaging parameters, including Luc expression by IVIC, tumor size and mice survival. Tumors are also analyzed by histology and expression of miR target genes accordingly.

b). The intrahepatic human HCC tumor model: In an effort to assess HCC growth in the liver, as occurs in most HCC cases and also in those escaping therapy, human HCC cells are injected into the spleen. Intrasplenic injection cause the migration of cells into the liver and growth of human HCC tumors in the mice livers. Consequently, miR activator agents are administered to induce an effect. The readouts for these experiments are similar to those in the subcutaneous model, above.

4. Determining the Anti-Metastatic Effect of Tumor Suppressive miRs Against Human HCC:

Although in most HCC patients, their HCC growth and escape from therapy—recurrence, is usually intrahepatic some patients develop distant metastasis. To model this, the three human HCC cells used in above are each injected into the tail vein of SCID mice to establish human HCC metastasis in the lungs. Once the tumors are established, (as determined by the use of IVIC system), miR activator agent are administered. HCC growth, clinical measures and biology are monitored as described above.

5. Determining the Anti-Metastatic Effect of Tumor Suppressive miRs Against Human HCC:

To this aim, splenic injection of human HCC cells into SCID mice to cause migration into the liver of tested mice via the portal system is used to establish an animal model whereby the impact on tumor cells is readily amenable for testing. At least three different HCC cell lines are used for these experiments. The injected HCC cells harbor a GFP/Luc construct, which is stably transfected into the CCR5Δ32 locus with a CRISPR/Cas9 system to ease comparison of effect. Once the human cells grow in the mouse liver, as determined by using the IVIC imaging system detecting luciferase, animals are exposed to suitable agents that can increase the levels and/or secretion of tumor suppressive miRs. The readouts include IVIC monitoring, histology and survival. In addition, for collecting more anti-tumor data, cell lines harboring the "miR tester" construct are subcutaneously implanted in another set of animals to assess anti-tumor effects.

6. Assessing the Tumor Suppressive Impact of Secreted miRs on Metastatic Human HCC Cells In Vivo:

Metastasis is a primary killer in patients with cancer. To simulate metastasis, human HCC cells harboring the GFP/Luc expression vector integrated into the CCR5Δ32 locus are tail-vain injected to test mice. Once lung metastasis are generated (as determined using IVIC monitoring), mice are administered with the suitable tested miR agent stimulator(s). The readouts for these experiments include IVIC monitoring, histology and survival.

Reference is made to FIGS. 8A-D, which show the in-vivo effect of activation of RORα on the production, expression and secretion of tumor suppressor miR-122.

Figure 8A:
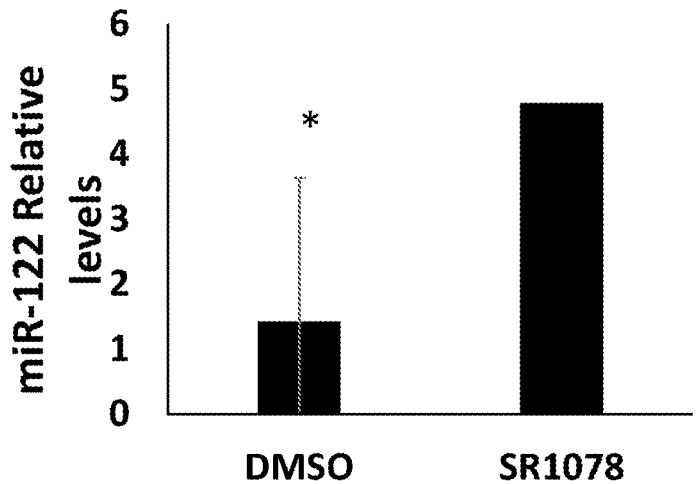
FIGS. 8A-D—Bar graphs showing the in-vivo effect of RORα agonist on the expression, secretion and activity of miR-122.

As shown in FIG. 8A—SR1078 agent (ROR alpha activator) was injected (1-5 µM) into BALB/C mice and was able to induce miR-122 expression within 3 hours, as indicated by the increased relative expression levels of miR-122 in the liver. miRNA-122 increased expression is in hepatocytes ("producing cells").

Figure 8B:
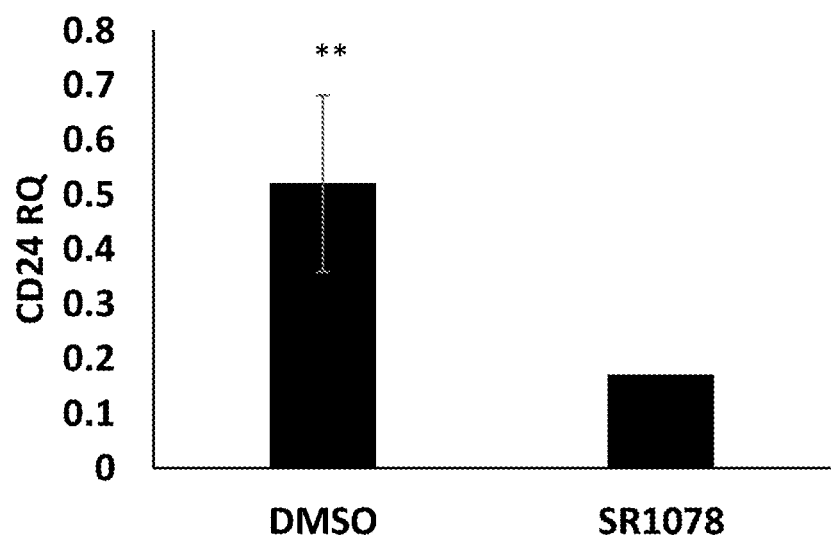
Figure 8C:
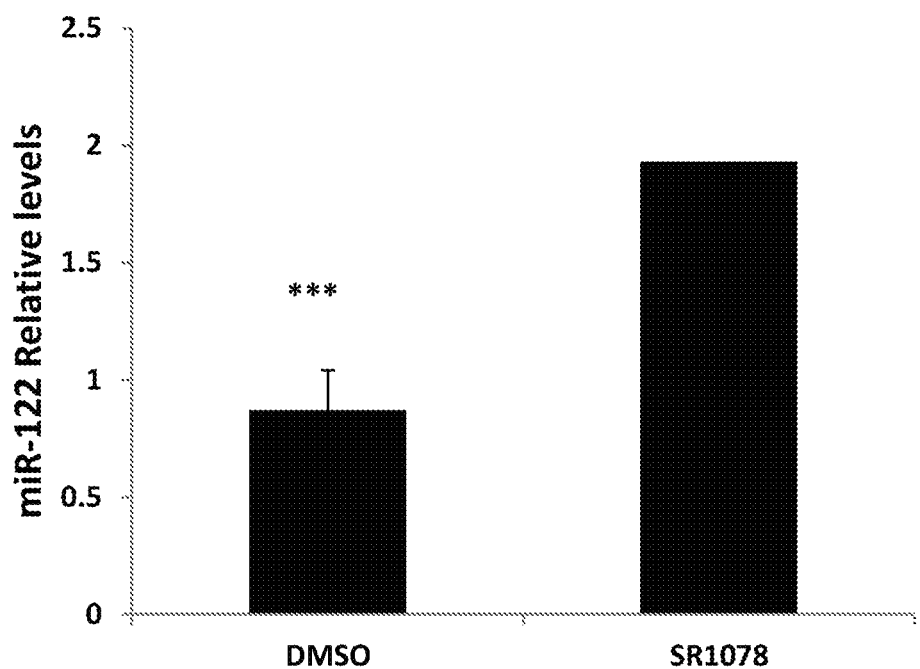
Figure 8D:
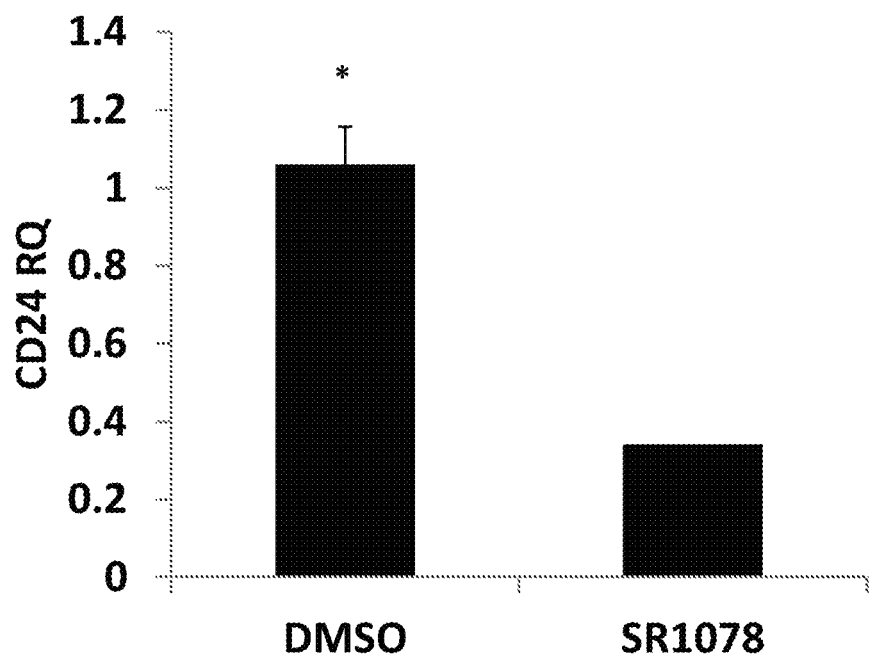

The CD24 gene, the protein product of which is expressed on hepatic progenitors, is a target of miR-122. As shown in FIG. 8B, the relative levels (RQ) of mRNA of CD24 in hepatic progenitor cells, are reduced, indicating that miR-122 is secreted from the producing cells hepatocytes and targets the expression CD24 on hepatic progenitors (target cells).

Similar effect is also apparent in measurements performed 6 hours after administration of the inducing agent, to three months old MDR2 knockout (KO) mice (which is a mice that develops liver cancer). This is presented in FIGS. 8C-D, which show the increase in relative levels of miR-122 (FIG. 8C) in liver extracts (hepatocytes) and the reciprocal reduction of CD24 relative expression levels (FIG. 8D), in progenitor cells.

Thus, the results clearly demonstrate that an agent administered in-vivo (RORα agonist) can induce expression of miRNA (in this example, miR-122) in producing cells (in this example, hepatocytes), which is then secreted and can act on target cells (in this example, progenitor cells), by affecting expression of target proteins (in this example, CD24).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method of treating hepatocellular carcinoma in a subject in need thereof, the method comprising administering to the subject a composition comprising a RORα agonist, selected from the group consisting of SR1078 and Lauric acid (LA), capable of increasing production or expression of one or more endogenous tumor suppressive miRNAs in one or more miRNA producing cells, wherein the one or more tumor suppressive endogenous miRNAs comprise miR-34a, such that the one or more endogenous tumor suppressive miRNAs affect one or more target hepatocellular carcinoma cells, thereby treating hepatocellular carcinoma in said subject.

2. The method of claim 1, wherein said increasing expression comprises inducing transcription of the one or more endogenous miRNAs in the one or more producing cells.

3. The method of claim 1, wherein the producing cell is a target cell.

4. The method of claim 1, wherein the target cancer cell is different than the producing cell.

5. The method of claim 1, wherein the target cancer cell resides in a different tissue than the tissue in which the producing cell resides.

6. The method of claim 1, wherein the target cancer cell is located at a remote location relative to the producing cell.

7. The method of claim 1, wherein the miRNA is secreted from the producing cell.

8. The method of claim 1, wherein the miRNA is secreted from the producing cell in apoptotic bodies, Ribonuclear complex (RNP), a lipid vesicle or any combination thereof.

9. The method of claim 8, wherein the lipid vesicle comprises exosomes.

10. The method of claim 1, wherein the target cancer cells are metastatic cancer cells.

11. The method of claim 1, wherein the target cancer cells are cells derived from hepatocellular carcinoma cells.

12. The method of claim 1, wherein the tumor suppressive miRNAs further comprise a miRNA selected from the group consisting of: miR-122, miR-16, miR-19a, miR-23a, miR-29c, miR-98, miR-99a, miR-101, miR-122*, miR-124, miR-125b, miR-126, miR-127, miR-133a, miR-133b, miR-143, miR-145, miR-146b, miR-153, miR-154, miR-190a, miR-195, miR-200a, miR-206, miR-214, miR-217, miR-296, miR-302b, miR-320a, miR-338-3p, miR-363-3p, miR-375, miR-379, miR-381, miR-384, miR-429, miR-449, miR-451, miR-486, miR-489, miR-497, miR-503, miR-506, miR-511, miR-542-3p, miR-599, miR-613, miR-718, miR-874, -miR 922, and miR-4510.

13. The method of claim 1, wherein the tumor suppressive miRNA is miR-122 and miR-34a.

14. The method of claim 1, wherein the composition is a pharmaceutical composition.

\* \* \* \* \*